US00RE48250E

(19) United States
(12) Reissued Patent
McClintock et al.

(10) Patent Number: US RE48,250 E
(45) Date of Reissued Patent: Oct. 13, 2020

(54) ROD REDUCER, COMPRESSOR, DISTRACTOR SYSTEM

(71) Applicant: K2M, Inc., Leesburg, VA (US)

(72) Inventors: Larry E. McClintock, Gore, VA (US); Clint Boyd, Winchester, VA (US)

(73) Assignee: K2M, Inc., Leesburg, VA (US)

(21) Appl. No.: 16/545,644

(22) Filed: Aug. 20, 2019

Related U.S. Patent Documents

Reissue of:
(64) Patent No.: 9,737,351
Issued: Aug. 22, 2017
Appl. No.: 14/828,909
Filed: Aug. 18, 2015

U.S. Applications:
(62) Division of application No. 13/741,934, filed on Jan. 15, 2013, now Pat. No. 9,125,703.
(Continued)

(51) Int. Cl.
*A61B 17/88* (2006.01)
*A61B 17/70* (2006.01)

(52) U.S. Cl.
CPC ..... *A61B 17/88* (2013.01); *A61B 17/708* (2013.01); *A61B 17/7079* (2013.01); *A61B 17/7085* (2013.01); *A61B 17/7086* (2013.01)

(58) Field of Classification Search
CPC ... A61B 17/88; A61B 17/708; A61B 17/7079; A61B 17/7085; A61B 17/7086
See application file for complete search history.

(56) References Cited

U.S. PATENT DOCUMENTS 1,920,821 A * 8/1933 Wassenaar ..... A61B 17/6408 606/86 R
3,244,170 A * 4/1966 McElvenny ..... A61B 17/7225 606/105
(Continued)

FOREIGN PATENT DOCUMENTS

DE 29710979 U1 8/1997
DE 19726754 A1 2/1999
(Continued)

OTHER PUBLICATIONS

Charles Hartjen; The Atavi System, Surgical Technique Brochure. Endius, p. 1-17, undated.
(Continued)

*Primary Examiner* — David O Reip
(74) *Attorney, Agent, or Firm* — Lerner, David, Littenberg, Krumholz & Mentlik, LLP

(57) ABSTRACT

A compressor/distractor system for operating on a spine is disclosed. The system includes two rod reducers which each advance a spinal rod into the shoulder portion of a pedicle screw. Each rod reducer includes an inner member, an outer member, and a pair of gripping members. Each outer member receives and advances the spinal rod into the pedicle screw. The outer member also includes a through slot which receives the proximal end of each of the pair of gripping members which may limit the longitudinal translation of the outer member with respect to the inner member. The compressor/distractor system may include a compressor/distractor device which has a compressing, a distracting, and a neutral configuration. A method for using the minimally invasive rod reducers with the compressor/distractor system to secure at least two pedicle screws in desired positions on a spinal rod is also disclosed.

34 Claims, 11 Drawing Sheets

Related U.S. Application Data

(60) Provisional application No. 61/586,928, filed on Jan. 16, 2012.

(56) References Cited

U.S. PATENT DOCUMENTS 3,997,138 A 12/1976 Crock et al.
4,263,899 A 4/1981 Burgin
4,382,438 A 5/1983 Jacobs
4,409,968 A 10/1983 Drummond
4,411,259 A 10/1983 Drummond
4,957,495 A 9/1990 Kluger
5,010,879 A 4/1991 Moriya et al.
5,059,194 A 10/1991 Michelson
5,167,662 A * 12/1992 Hayes ..... A61B 17/7076 606/151
5,242,443 A 9/1993 Kambin
5,281,223 A 1/1994 Ray
5,385,565 A 1/1995 Ray
5,478,340 A 12/1995 Kluger
5,487,743 A 1/1996 Laurain et al.
5,529,571 A 6/1996 Daniel
5,591,167 A 1/1997 Laurain et al.
5,672,175 A * 9/1997 Martin ..... A61B 17/025 606/105
5,685,826 A 11/1997 Bonutti
5,704,937 A * 1/1998 Martin ..... A61B 17/025 606/102
RE36,221 E 6/1999 Breard et al.
5,944,658 A 8/1999 Koros et al.
6,090,113 A 7/2000 Le Couedic et al.
6,123,707 A 9/2000 Wagner
6,146,386 A 11/2000 Blackman et al.
6,200,322 B1 3/2001 Branch et al.
6,485,518 B1 11/2002 Cornwall et al.
6,506,151 B2 1/2003 Estes et al.
6,530,929 B1 3/2003 Justis et al.
6,616,605 B2 9/2003 Wright et al.
6,616,666 B1 9/2003 Michelson
6,616,667 B1 9/2003 Steiger et al.
6,712,818 B1 3/2004 Michelson
6,849,064 B2 2/2005 Hamada
6,929,606 B2 8/2005 Ritland
7,008,422 B2 3/2006 Foley et al.
7,011,660 B2 3/2006 Sherman et al.
7,083,621 B2 8/2006 Shaolian et al.
7,160,300 B2 1/2007 Jackson
7,179,261 B2 2/2007 Sicvol et al.
7,188,626 B2 3/2007 Foley et al.
7,250,052 B2 7/2007 Landry et al.
7,462,182 B2 12/2008 Lim
7,491,208 B2 2/2009 Pond, Jr. et al.
7,591,836 B2 9/2009 Dick et al.
7,625,379 B2 12/2009 Puno et al.
7,651,502 B2 1/2010 Jackson
7,655,008 B2 2/2010 Lenke et al.
7,666,189 B2 2/2010 Gerber et al.
7,794,464 B2 9/2010 Bridwell et al.
7,854,751 B2 12/2010 Sicvol et al.
7,922,749 B2 4/2011 Dewey
7,927,334 B2 4/2011 Miller et al.
7,946,982 B2 5/2011 Hamada
7,951,168 B2 5/2011 Chao et al.
7,951,175 B2 5/2011 Chao et al.
7,955,355 B2 6/2011 Chin
7,981,115 B2 * 7/2011 Justis ..... A61B 90/06 606/102
7,988,694 B2 8/2011 Barrus et al.
8,002,798 B2 8/2011 Chin et al.
8,007,516 B2 8/2011 Chao et al.
8,147,524 B2 4/2012 Piza Vallespir
8,157,809 B2 4/2012 Butters et al.
8,192,438 B2 6/2012 Garamszegi
8,206,395 B2 6/2012 McLean et al.
8,221,426 B2 * 7/2012 Justis ..... A61B 17/708 606/86 A
8,221,474 B2 7/2012 Bridwell et al.
8,230,863 B2 7/2012 Ravikumar et al.
8,277,453 B2 10/2012 Kave et al.
8,298,138 B2 10/2012 Gorek et al.
8,303,595 B2 11/2012 Jones
8,308,729 B2 11/2012 Nunley et al.
8,308,774 B2 11/2012 Hoffman et al.
8,506,574 B2 8/2013 Butters et al.
8,545,505 B2 10/2013 Sandstrom et al.
8,702,713 B2 4/2014 Nayet et al.
8,764,757 B1 * 7/2014 Tumialan ..... A61F 2/4455 600/210
8,784,424 B2 * 7/2014 Tsuang ..... A61B 17/1671 606/86 A
8,894,655 B2 11/2014 Fallin et al.
8,915,925 B2 12/2014 Butters et al.
9,125,703 B2 9/2015 McClintock et al.
9,179,947 B2 * 11/2015 Bass ..... A61B 17/025
9,345,463 B2 5/2016 Butters et al.
2002/0052603 A1 5/2002 Nichols et al.
2003/0055430 A1 3/2003 Kim
2003/0073998 A1 4/2003 Pagliuca et al.
2003/0187436 A1 10/2003 Bolger et al.
2004/0034351 A1 2/2004 Sherman et al.
2004/0138662 A1 7/2004 Landry et al.
2004/0143265 A1 7/2004 Landry et al.
2004/0147928 A1 7/2004 Landry et al.
2004/0172022 A1 9/2004 Landry et al.
2004/0215190 A1 10/2004 Nguyen et al.
2004/0230191 A1 11/2004 Frey et al.
2004/0260287 A1 12/2004 Ferree
2004/0267275 A1 12/2004 Cournoyer et al.
2005/0010220 A1 1/2005 Casutt et al.
2005/0010221 A1 1/2005 Dalton
2005/0021030 A1 1/2005 Pagliuca et al.
2005/0021031 A1 1/2005 Foley et al.
2005/0038436 A1 2/2005 Michelson
2005/0070917 A1 3/2005 Justis
2005/0090822 A1 4/2005 DiPoto
2005/0090833 A1 4/2005 DiPoto
2005/0131421 A1 6/2005 Anderson et al.
2005/0131422 A1 * 6/2005 Anderson ..... A61B 17/7079 606/104
2005/0154389 A1 7/2005 Selover et al.
2005/0245928 A1 * 11/2005 Colleran ..... A61B 17/708 606/90
2006/0004380 A1 * 1/2006 DiDomenico ..... A61B 17/0819 606/105
2006/0111714 A1 5/2006 Foley
2006/0200132 A1 * 9/2006 Chao ..... A61B 17/708 606/86 A
2006/0200135 A1 9/2006 Sherman et al.
2006/0247645 A1 * 11/2006 Wilcox ..... A61B 17/025 606/86 R
2006/0247649 A1 * 11/2006 Rezach ..... A61B 17/7077 606/90
2006/0264934 A1 * 11/2006 Fallin ..... A61B 17/8863 606/86 A
2007/0055247 A1 3/2007 Jahng
2007/0162009 A1 7/2007 Chao et al.
2007/0162010 A1 7/2007 Chao et al.
2007/0213715 A1 * 9/2007 Bridwell ..... A61B 17/025 606/264
2007/0233079 A1 * 10/2007 Fallin ..... A61B 17/7085 606/86 A
2008/0015601 A1 1/2008 Castro et al.
2008/0077155 A1 * 3/2008 Diederich ..... A61B 17/708 606/105
2008/0119862 A1 * 5/2008 Wicker ..... A61B 17/708 606/99
2008/0125789 A1 * 5/2008 Butters ..... A61B 17/025 606/105
2008/0172062 A1 * 7/2008 Donahue ..... A61B 17/708 606/104
2009/0018593 A1 1/2009 Barrus et al.

(56) References Cited

U.S. PATENT DOCUMENTS

2009/0062857 A1* 3/2009 Ramsay ..... A61B 17/1735 606/246
2009/0082775 A1* 3/2009 Altarac ..... A61B 17/025 606/90
2009/0138056 A1* 5/2009 Anderson ..... A61B 17/7074 606/86 A
2009/0143828 A1* 6/2009 Stad ..... A61B 17/7085 606/86 A
2009/0149892 A1* 6/2009 Stad ..... A61B 17/7077 606/86 A
2009/0157125 A1* 6/2009 Hoffman ..... A61B 17/7091 606/86 A
2009/0171391 A1* 7/2009 Hutton ..... A61B 17/7032 606/246
2009/0228053 A1* 9/2009 Kolb ..... A61B 17/7076 606/86 A
2009/0259262 A1* 10/2009 Nayet ..... A61B 17/7079 606/86 A
2009/0326586 A1* 12/2009 Duarte ..... A61B 17/7089 606/264
2010/0024487 A1* 2/2010 Khoo ..... A61B 17/708 66/90
2010/0030283 A1* 2/2010 King ..... A61B 17/7037 606/86 A
2010/0036443 A1* 2/2010 Hutton ..... A61B 17/7032 606/86 R
2010/0324610 A1 12/2010 Bridwell et al.
2010/0331849 A1* 12/2010 Riesinger ..... A61B 17/7077 606/90
2011/0077690 A1* 3/2011 Shin ..... A61B 17/7074 606/278
2011/0106082 A1* 5/2011 Kave ..... A61B 17/708 606/70
2011/0130793 A1* 6/2011 Woolley ..... A61B 17/0206 606/279
2011/0137358 A1* 6/2011 Manninen ..... A61B 17/7079 606/86 R
2011/0152940 A1* 6/2011 Frigg ..... A61B 17/7002 606/264
2011/0172714 A1 7/2011 Boachie-Adjei et al.
2011/0172723 A1* 7/2011 Miller ..... A61B 17/7088 606/86 A
2011/0196426 A1* 8/2011 Peukert ..... A61B 17/7083 606/279
2011/0257692 A1* 10/2011 Sandstrom ..... A61B 17/7085 606/86 A
2011/0282402 A1 11/2011 Chao et al.
2011/0295328 A1 12/2011 Woolley et al.
2011/0313477 A1* 12/2011 McLean ..... A61B 17/7011 606/86 A
2011/0319938 A1* 12/2011 Piza Vallespir .... A61B 17/7076 606/264
2012/0031792 A1* 2/2012 Petit ..... A61B 17/708 206/438
2012/0035668 A1* 2/2012 Manninen ..... A61B 17/7037 606/305
2012/0078308 A1* 3/2012 Dziedzic ..... A61B 17/7086 606/264
2012/0083853 A1* 4/2012 Boachie-Adjei ... A61B 17/7038 606/86 A
2012/0116467 A1 5/2012 King et al.
2012/0191137 A1 7/2012 Butters et al.
2012/0191143 A1* 7/2012 Nayet ..... A61B 17/708 606/86 A
2012/0197297 A1* 8/2012 Bootwala ..... A61B 17/7077 606/246
2012/0239096 A1* 9/2012 Gleeson ..... A61B 17/708 606/86 A
2012/0239097 A1* 9/2012 Garamszegi ..... A61B 17/7086 606/86 A
2012/0271365 A1* 10/2012 Daubs ..... A61B 17/7086 606/86 A
2012/0323279 A1* 12/2012 Tsuang ..... A61B 17/7002 606/279
2013/0012999 A1* 1/2013 Petit ..... A61B 17/7076 606/279
2013/0046345 A1* 2/2013 Jones ..... A61B 17/7037 606/266
2013/0096635 A1* 4/2013 Wall ..... A61B 17/7085 606/305
2013/0096637 A1* 4/2013 Richelsoph ..... A61B 17/7089 606/86 A
2013/0110184 A1* 5/2013 Wing ..... A61B 17/708 606/86 A
2013/0172947 A1* 7/2013 Greenberg ..... A61B 17/708 606/86 A
2013/0184763 A1* 7/2013 McClintock ..... A61B 17/88 606/279
2013/0238037 A1* 9/2013 Stad ..... A61B 17/708 606/86 A
2013/0245692 A1* 9/2013 Hayes ..... A61B 17/708 606/279
2013/0245694 A1* 9/2013 Choi ..... A61B 17/708 606/279
2013/0274804 A1 10/2013 Hutton et al.
2013/0289633 A1* 10/2013 Gleeson ..... A61B 17/7074 606/86 A
2014/0018860 A1 1/2014 Butters et al.
2014/0031828 A1* 1/2014 Patel ..... A61B 17/025 606/90
2014/0039557 A1 2/2014 Stad et al.
2014/0039567 A1* 2/2014 Hoefer ..... A61B 17/708 606/86 A
2014/0046372 A1* 2/2014 Ibrahim ..... A61B 17/8605 606/250
2014/0052139 A1 2/2014 Manninen
2014/0074106 A1* 3/2014 Shin ..... A61B 17/7079 606/104
2014/0074171 A1 3/2014 Hutton et al.
2014/0100617 A1 4/2014 Sandstrom et al.
2014/0100618 A1 4/2014 Kolb et al.
2014/0107707 A1* 4/2014 Rovner ..... A61B 17/7034 606/264
2014/0114354 A1* 4/2014 May ..... A61B 17/708 606/246
2014/0135855 A1* 5/2014 Jones ..... A61B 17/7091 606/86 A
2014/0163575 A1* 6/2014 Thoren ..... A61B 17/7077 606/105
2014/0188182 A1 7/2014 Chao et al.
2014/0249591 A1* 9/2014 Peultier ..... A61B 17/7077 606/86 A
2014/0257312 A1* 9/2014 Solitario, Jr. ..... A61B 17/7079 606/90
2014/0277151 A1* 9/2014 Fowler ..... A61B 17/7074 606/265
2014/0277198 A1* 9/2014 Stad ..... A61B 17/7074 606/86 A
2014/0316475 A1* 10/2014 Parikh ..... A61B 17/7083 606/86 A
2015/0238235 A1* 8/2015 Tuten ..... A61B 17/7077 606/279
2016/0106408 A1* 4/2016 Ponmudi ..... A61B 17/025 606/90
2016/0262807 A1* 9/2016 Benson ..... A61B 17/7077
2016/0338683 A1 11/2016 Butters et al.

FOREIGN PATENT DOCUMENTS

DE 10027988 1/2002
EP 0528117 A2 2/1993
EP 0611116 A1 8/1994
EP 665731 8/1995
SU 839513 A1 6/1981
WO 9409726 A1 5/1994
WO 0141681 A1 6/2001
WO 04021899 A1 3/2004
WO 04037074 A2 5/2004

(56) References Cited

FOREIGN PATENT DOCUMENTS

| | | | |
|---|---|---|---|
| WO | 04041100 | A1 | 5/2004 |
| WO | 04080318 | A1 | 9/2004 |
| WO | 05018466 | A2 | 3/2005 |
| WO | 05023123 | A1 | 3/2005 |
| WO | 05032358 | A2 | 4/2005 |
| WO | 05060534 | A2 | 7/2005 |
| WO | 2006060430 | A1 | 6/2006 |

OTHER PUBLICATIONS

Diapason, Surgical Texchnique Catalog, Diapasan Spinal System, Jan. 2002.
Kambin et al, "Percutaneous Posterolateral Lumbar Discectomy and Decompression with a 6.9-millimeter cannula", The Journal of Bone and Joint Surgery, pp. 822-831, Jul. 1991.
Kambin, Minimally Invasive Techniques in Spinal Surgery Current Practice, Neurosurgical Focus, wwwspineuniversecom, 16 pages, printed Aug. 24, 2005.
Leu et al., Percutaneous Fusion of the Lumbar Spine, State of the Art Reviews, vol. 6, No. 3, pp. 593-604, Sep. 1992.
Pathfinder; Minimally Invasive Pedicie Fixation System. Spinal Concepts Product Brochure p. 1-4, May 2003.

* cited by examiner

ROD REDUCER, COMPRESSOR, DISTRACTOR SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application is *an application for the reissue of U.S. Pat. No. 9,737,351, which is* a divisional of U.S. patent application Ser. No. 13/741,934, filed [Jun.] *Jan.* 15, 2013, which claims the benefit of, and priority to, U.S. Provisional Application Ser. No. 61/586,928, filed on Jan. 16, 2012. The entire contents of each of the above applications are incorporated herein by reference.

BACKGROUND

Technical Field

The present disclosure relates to a system and method for operating on the spine. More particularly, the present disclosure relates to a minimally invasive rod reducer, compressor/distractor system, and a method for using the compressor/distractor system to deliver a spinal rod to the head of a pedicle screw.

Background of Related Art

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws are utilized to capture these rods and can be manufactured from any biocompatible material, including cobalt chrome, stainless steel, titanium, and PEEK. It is desired to perform these procedures in a minimally invasive manner to minimize pain and reduce recovery time for the patient. Therefore, a need exists for a minimally invasive rod reducer, compressor, distractor system that can deliver the rod into the head of the pedicle screw or bone anchor while maintaining the proper screw and rod construct alignment.

A rod reducer that is small enough in diameter to work with a minimally invasive retractor, such as the rod reducer disclosed in U.S. Patent Publication No. 2013/0046345, the contents of which are hereby incorporated by reference in their entirety and a minimally invasive retractor, such as the minimally invasive retractor disclosed in U.S. Pat. No. 7,846,093, the contents of which are hereby incorporated by reference in their entirety, are also disclosed.

SUMMARY

The present disclosure is directed towards a system for operating on the spine. The system includes pedicle screws, rod reducers, and a force applying device.

According to one aspect, the rod reducers include a proximal end and a distal end and define a longitudinal axis between the proximal and distal ends. The rod reducer includes an outer member and an inner member. The inner member is selectively attachable to the housing of the pedicle screw. The outer member is axially movable relative to the inner member when the inner member is secured to the housing of the pedicle screw to secure the spinal rod within the saddle of the housing of the pedicle screw. The outer member includes a proximal segment and a distal segment. The proximal segment is rotatable for axially translating the distal segment. The distal segment is engageable with the spinal rod to secure the spinal rod within the saddle upon the axial translation of the distal segment. The proximal segment independently rotates relative to the distal segment. The rod reducer includes a pair of gripping members configured to engage the housing of the pedicle screw. The pair of gripping members is positioned between the inner and outer members of the rod reducer.

The handle assembly is selectively engageable with the rod reducer to move the outer member of the rod reducer axially relative to the inner member of the rod reducer. The handle assembly is configured to rotate the outer member so that the rotational movement of the outer member axially moves the outer member relative to the inner member. The handle assembly includes a turning handle and an anti-torque handle. The anti-torque handle is selectively engageable with the proximal end of the rod reducer and the turning handle is selectively engageable with a proximal end of the anti-torque handle.

In another aspect, an embodiment of the system includes two rod reducers, a force applying device, and a fulcrum. The force applying device is configured for selectively engaging each rod reducer. The system may also include at least one minimally invasive retraction device.

In yet another aspect, the force applying device is a compressor/distractor device including a first hook member, a second hook member, and a body portion. The body portion has a first end and a track extending from the first end. The first end includes the first hook member in a fixed position. The first end may slidably receive the first hook member in a fixed position. The track includes a set of teeth and is configured for slidably receiving the second hook member.

The second hook member includes a switch assembly and a gear assembly. The second hook member traverses the track when the gear assembly is rotated. The gear assembly may also retain the second hook member within the track. The switch assembly permits the second hook member to traverse the track in a desired direction, towards the first hook member or away from the first hook member. The switch assembly may also restrain the second hook member from traversing the track in an undesired direction.

The first and second hook members may be configured in a compressing configuration to engage the two rod reducers such that rod reducers are between the hook members. The first and second hook members may also be configured in a distracting configuration to engage the rod reducers such that the hook members are between the rod reducers.

The fulcrum is configured to receive the proximal segment of the outer member of each rod reducer and remain in a fixed position on the longitudinal axis of each rod reducer.

According to still another aspect, a method for compressing or distracting vertebrae including two minimally invasive rod reducers, a compressor/distractor system, a spinal rod, and two pedicle screws. The method includes the steps of accessing the spinal area of a patient having at least two pedicle screws secured to respective vertebrae, engaging each pedicle screw with a rod reducer, advancing the spinal rod into the head of each pedicle screw, attaching a compressor/distractor device to each rod reducer, inserting a set screw through each rod reducer, manipulating the compressor/distractor device, and securing the spinal rod to each pedicle screw.

The method may also include the step of attaching a fulcrum to the proximal segment of each outer member before rotating the gear assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION OF THE DRAWINGS

Figures 1A, 1B, 1C:
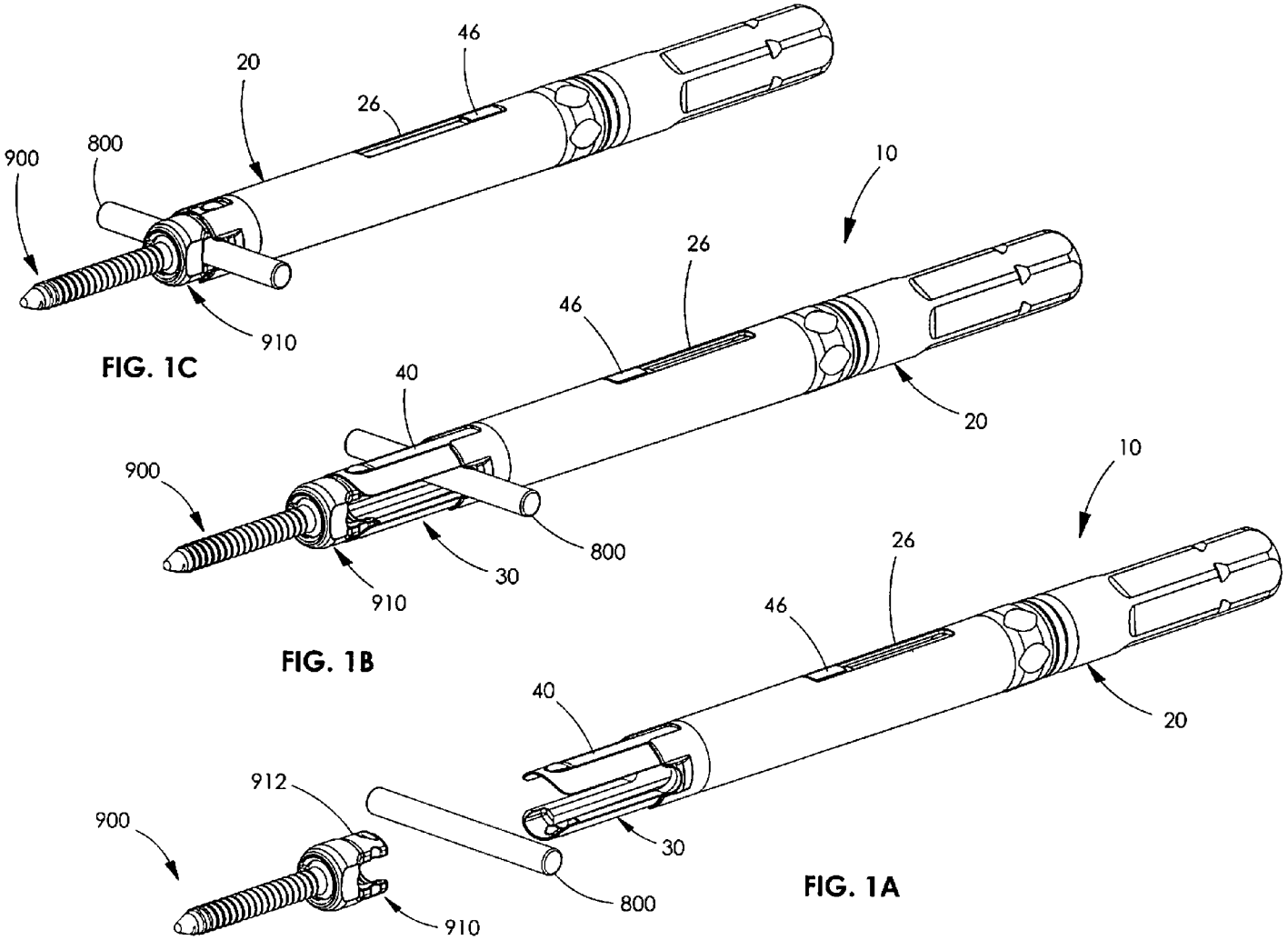
FIG. 1A is a perspective view of a minimally invasive rod reducer in accordance with the principles of the present disclosure before engagement with a rod and a pedicle screw.
FIG. 1B is a perspective view of the rod reducer of FIG. 1A after initial engagement of the rod and pedicle screw.
FIG. 1C is a perspective view of the rod reducer of FIG. 1B after the rod has been received by the shoulder portion of the pedicle screw
Figure 2:
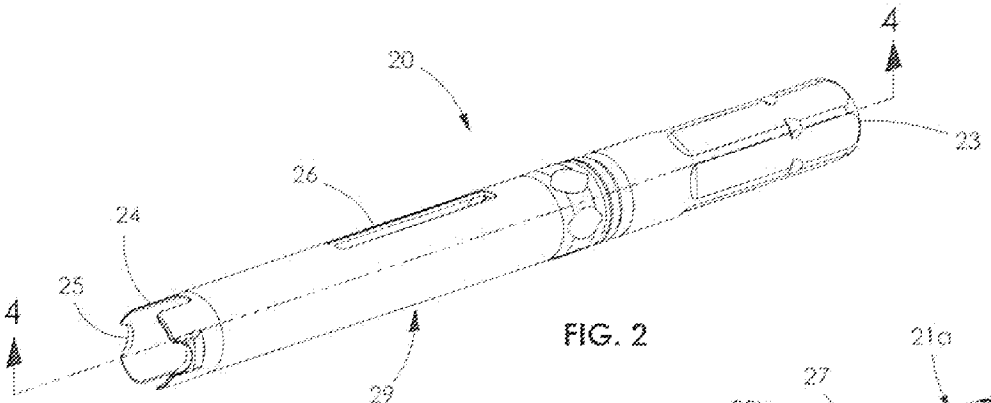
FIG. 2 is a perspective view of the outer member of FIG. 1A.
Figure 3:
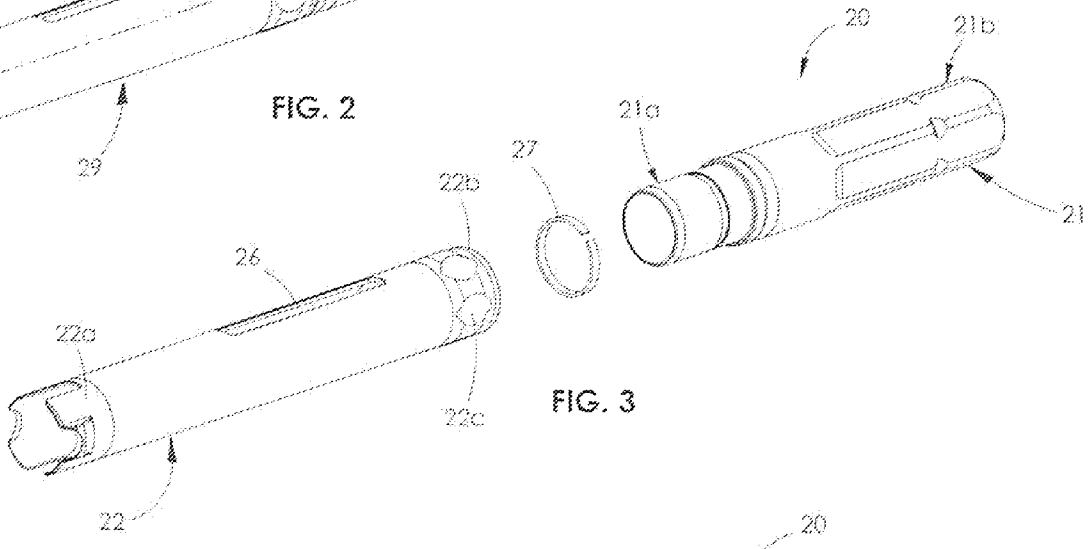
FIG. 3 is a exploded view of the outer member of FIG. 2.
Figure 4:
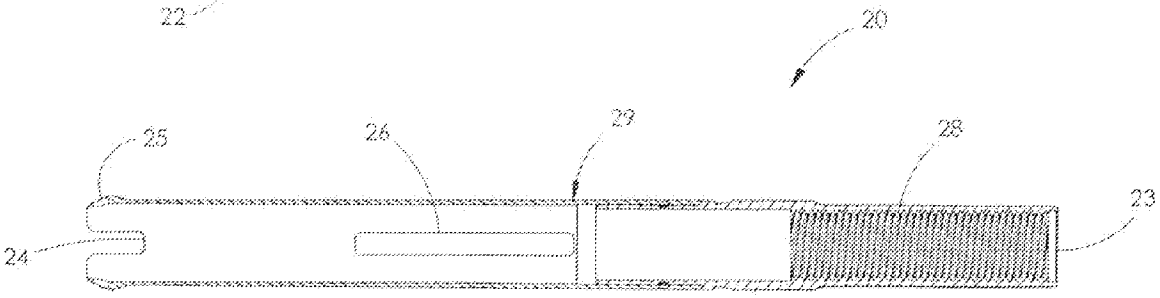
FIG. 4 is a bottom cross-sectional view of the outer member of FIG. 2 taken along the section line 4-4.
Figure 5:
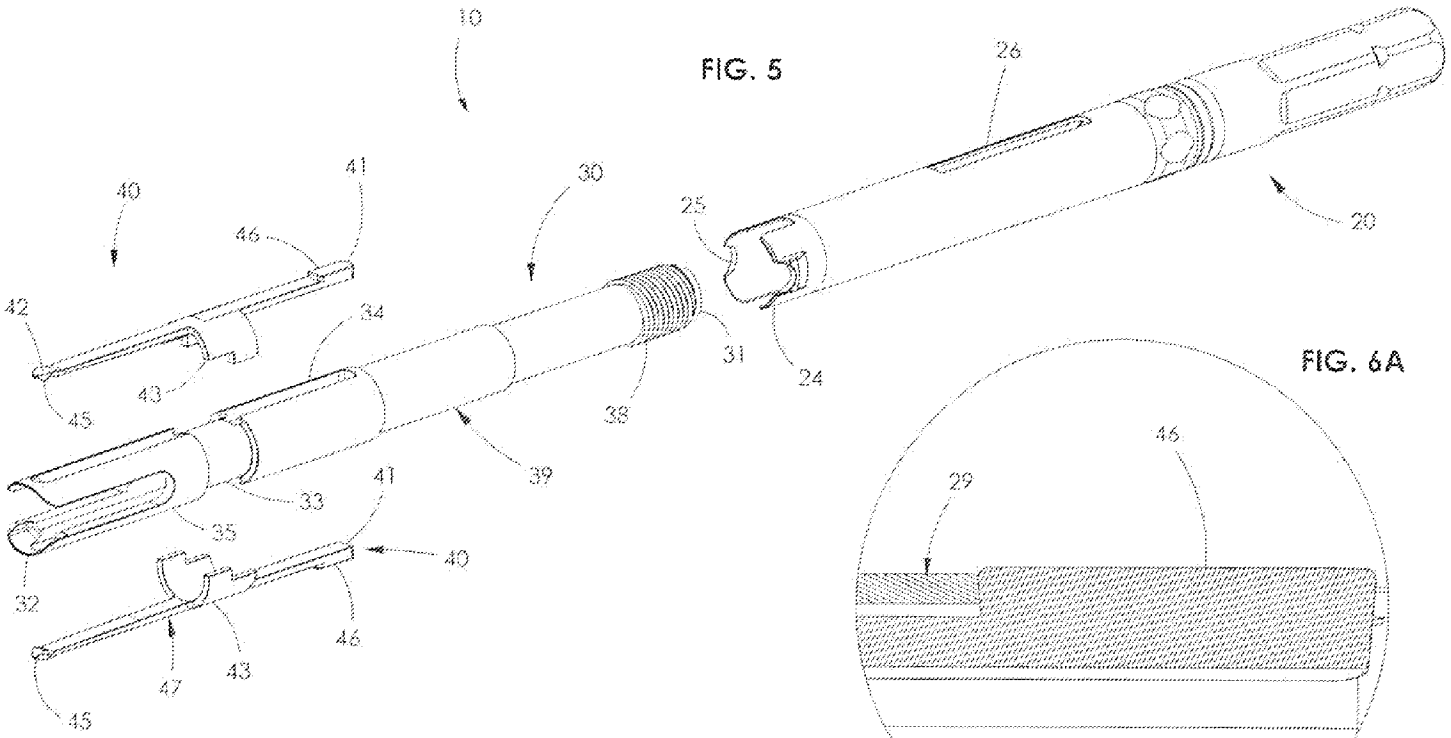
FIG. 5 is an exploded view of the rod reducer of FIG. 1A.
Figure 6A:
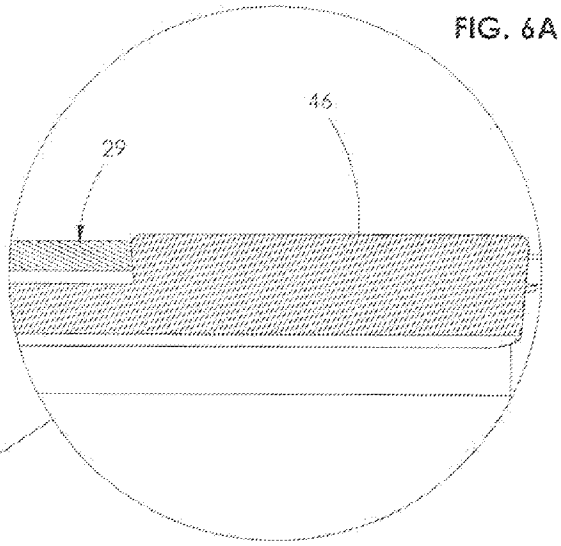
FIG. 6A is an enlarged view of the detail area 6A of FIG. 6.
Figure 6:
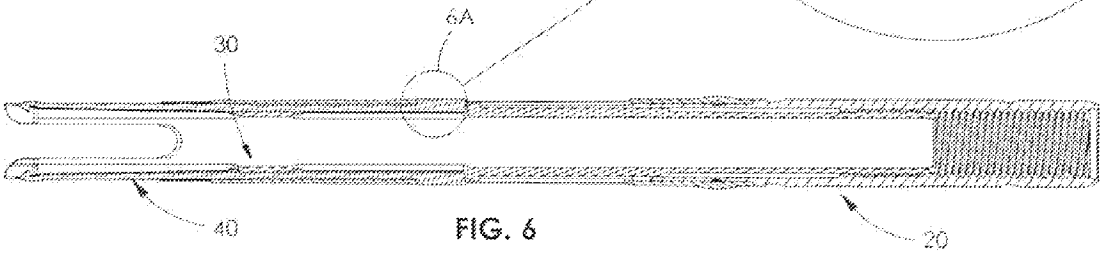
FIG. 6 is a side cross-sectional view of the of the rod reducer of FIG. 1A.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" or "cranial" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Turning now to FIGS. 2-6A, a rod reducer 10 includes an outer member 20, an inner member 30, and a pair of gripping members 40, such as the rod reducer disclosed in U.S. patent application Ser. No. 13/595,533 which is incorporated by reference. Outer member 20 includes a proximal segment 21, a distal segment 22, and a ring member 27 that is disposed between proximal and distal segments 21, 22. Proximal segment 21 includes an engaging portion 21a at a distal end of proximal segment 21 and a gripping portion 21b at a proximal end of proximal segment 21. An inner surface 28 of proximal segment 21 is threaded. Distal segment 22 defines a slot 26 therethrough and includes a reducing portion 22a at a distal end of distal segment 22 and a receiving portion 22b at a proximal end of distal segment 22. Receiving portion 22b includes a plurality of gripping features 22c on an outer surface of receiving portion 22b. A pair of rod engaging slots 25 and a pair of gripping member receiving slots 24 are defined through reducing portion 22a. Receiving portion 22b of distal segment 22 is configured to receive engaging portion 21a of proximal segment 21 so that ring member 27 is disposed between proximal and distal segments 21, 22. The components of outer member 20 may be integrally formed or assembled.

Inner member 30 includes an elongate body member 39 that defines an annular recess 33 configured to receive the pair of gripping members 40 so that the gripping members 40 are disposed in opposition on the elongate body member 39. Inner member 30 includes a pair of arms 32 supported on a distal end of elongate body member 39. A proximal end of elongate body member 39 has a threaded arrangement 38 that mates with threaded inner surface 28 of proximal segment 21 of outer member 20 to axially advance outer member 20 relative to inner member 30 as will be described in greater detail below.

Each gripping member 40 includes a body 47 having a supporting member 43, a proximal finger 46, and a distal finger 45. Supporting member 43 is configured to engage annular recess 33 of inner member 30 to support body 47 of each gripping member 40 on inner member 30. Proximal finger 46 extends proximally from supporting member 43 and is slidably positionable within slot 26 of outer member 20. Distal finger 45 extends distally from supporting member 43 and is positionable between an arm 32 of inner member 30 and reducing portion 22a of outer member 20 so that distal finger 45 is substantially aligned with a gripping member receiving slot 24 of reducing portion 22a.

As illustrated in FIGS. 1A-1C, outer member 20 of rod reducer 10 is disposed in a proximal position relative to inner member 30 of rod reducer 10, distal fingers 45 of gripping member 40 of rod reducer 10 are secured to an outer surface of pedicle screw head 910. Proximal segment 21 of outer member 20 may then be rotated by virtue of the threaded arrangement between outer member 20 and inner member 30 for axially advancing distal segment 22 of outer member 20 relative to inner member 30 and proximal segment 21. Proximal segment 21 remains axially fixed when rotated. Notably, as proximal segment 21 rotates, distal segment 22 remains radially fixed as distal segment 22 axially translates relative to inner member 30 and proximal segment 21. Outer member 20 approximates a spinal rod 800 positioned between rod reducer 10 and pedicle screw 900 as outer member 20 is advanced toward pedicle screw 900 to secure spinal rod 800 within a saddle 912 of pedicle screw 900. As outer member 20 advances distally, a proximal end of slot 26 of outer member 20 approximates a proximal end of proximal fingers 46 of gripping member 40.

Figure 7B:
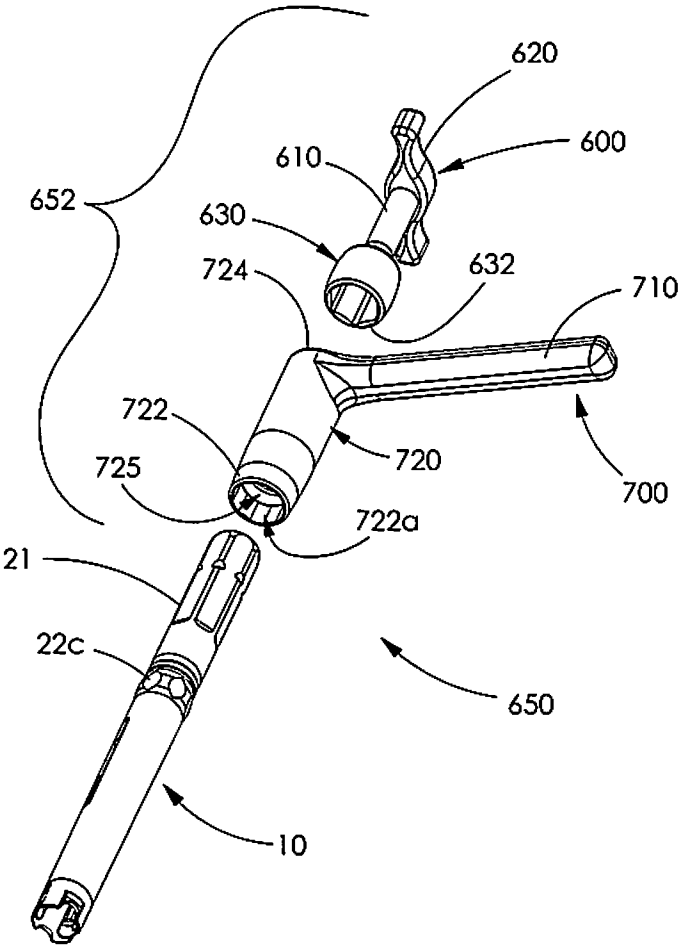
FIG. 7B is an exploded view of FIG. 7A.
Figure 7A:
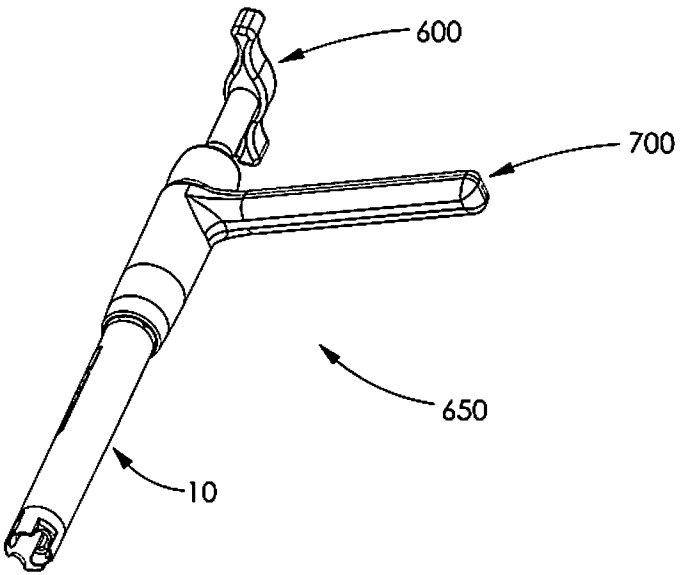
FIG. 7A is a perspective view of the outer member of FIG. 2 engaged with a turning handle and an anti-torque handle.

Turning now to FIGS. 7A and 7B, a rod reducer and handle assembly 650 includes the rod reducer 10 and a handle assembly 652. Handle assembly 652 includes a turning handle 600 and an anti-torque handle 700 that are selectively connectable to gripping portion 21b and gripping features 22c respectively on rod reducer 10. Turning handle 600 includes a shaft 610, a handle 620, and a socket 630 that defines an opening 632. Opening 632 is configured to receive a proximal end of gripping portion 21b of rod reducer 10. Handle 620 is secured to a proximal end of shaft 610 and a socket 630 that may be integrally formed is secured to a distal end of shaft 610. Anti-torque handle 700 includes a shaft 720 and a handle 710 that may be integrally formed. Shaft 720 includes a socket 722 that defines an opening 722a at a distal end of socket 722. Opening 722a is disposed in communication with a lumen 725 defined within shaft 720 and another opening 724 disposed at a proximal end of shaft 720 so that anti-torque handle 700 may slide over gripping portion 21b of rod reducer 10 and engage with gripping feature 22c of rod reducer 10 to prevent rotational movement of distal segment 22 of outer member 20 of rod reducer 10.

Thus, if needed, either or both the turning handle 600 and the anti-torque handle 700 may be used to facilitate the rotational movement of outer member 20 relative to inner member 30. In particular, rotation of turning handle 600 imparts rotational movement to proximal segment 21 of outer member 20 and anti-torque handle 700 imparts counter rotational movement to distal segment 22 of outer member 20 so that proximal segment 21 rotates and distal segment 22 axially translates without rotating. As appreciated, anti-torque handle 700 is configured to limit the amount of torque imparted from the rotational movement imparted by turning handle 600 to prevent undesirable torquing of the outer member 20. More particularly, anti-torque handle 700 slides down over the outer surface of outer member 20 of rod reducer 10 so that a distal end of anti-torque handle 700 engages distal segment 22 of outer member 20 and a proximal end of proximal segment 21 of outer member 20 is exposed for engagement with turning handle 600. Meanwhile, since gripping member 40 is secured within annular recess 33 of inner member 30 such that proximal finger 46 of gripping member 40 is supported in slot 26 of distal segment 22 of outer member 20, the engagement of anti-torque handle 700 with gripping feature 22c of distal segment 22 of outer member 20 prevents rotation of both distal segment 22 of outer member 20 and inner member 30 as proximal segment 21 of outer member 20 is rotated with turning handle 600. After spinal rod 800 is fully reduced into the saddle 910 of pedicle screw 900, turning handle 600 and anti-torque handle 700 may be removed and a set screw (not shown) may be inserted down an inner diameter of rod reducer 10 to lock spinal rod 800 into place. Alternatively, anti-torque handle 700 may also be used to prevent rotation when tightening the set screw after spinal rod 800 has been fully reduced. Rod reducer 10 may then be removed.

Figure 8:
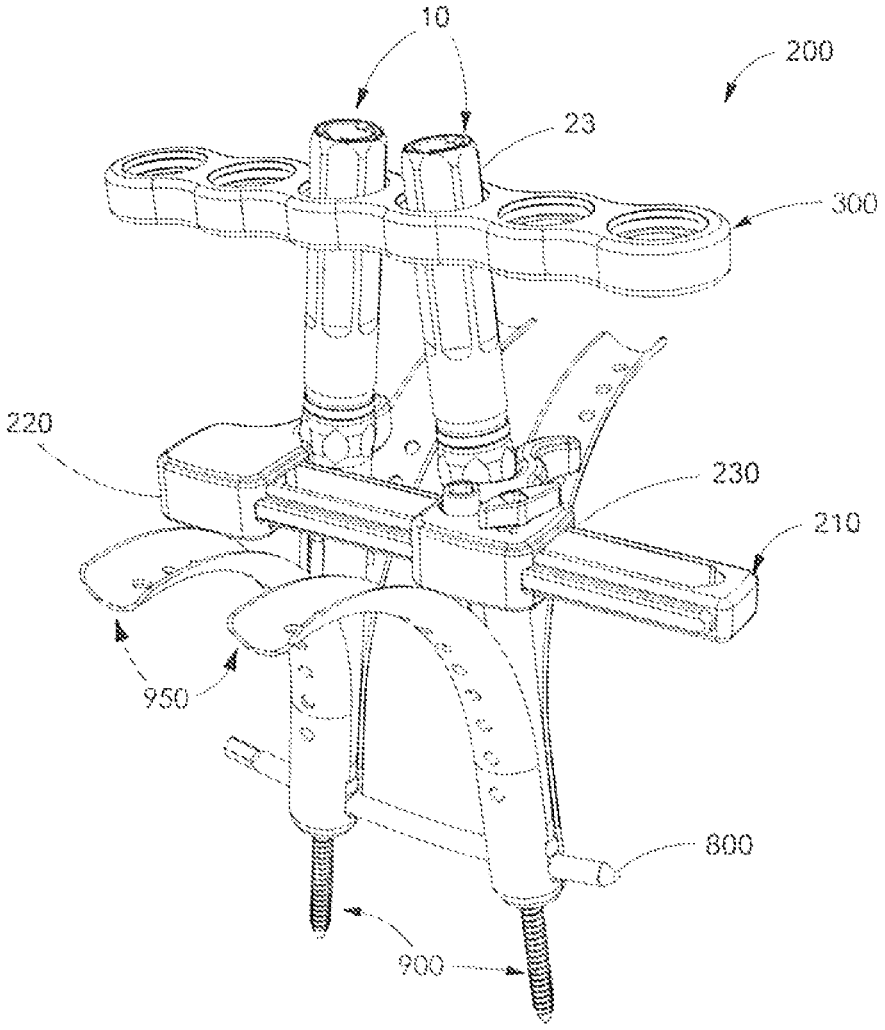
FIG. 8 is a perspective view of an embodiment of a compressor/distractor system in accordance with the principles of the present disclosure in a compressing configuration.
Figure 9:
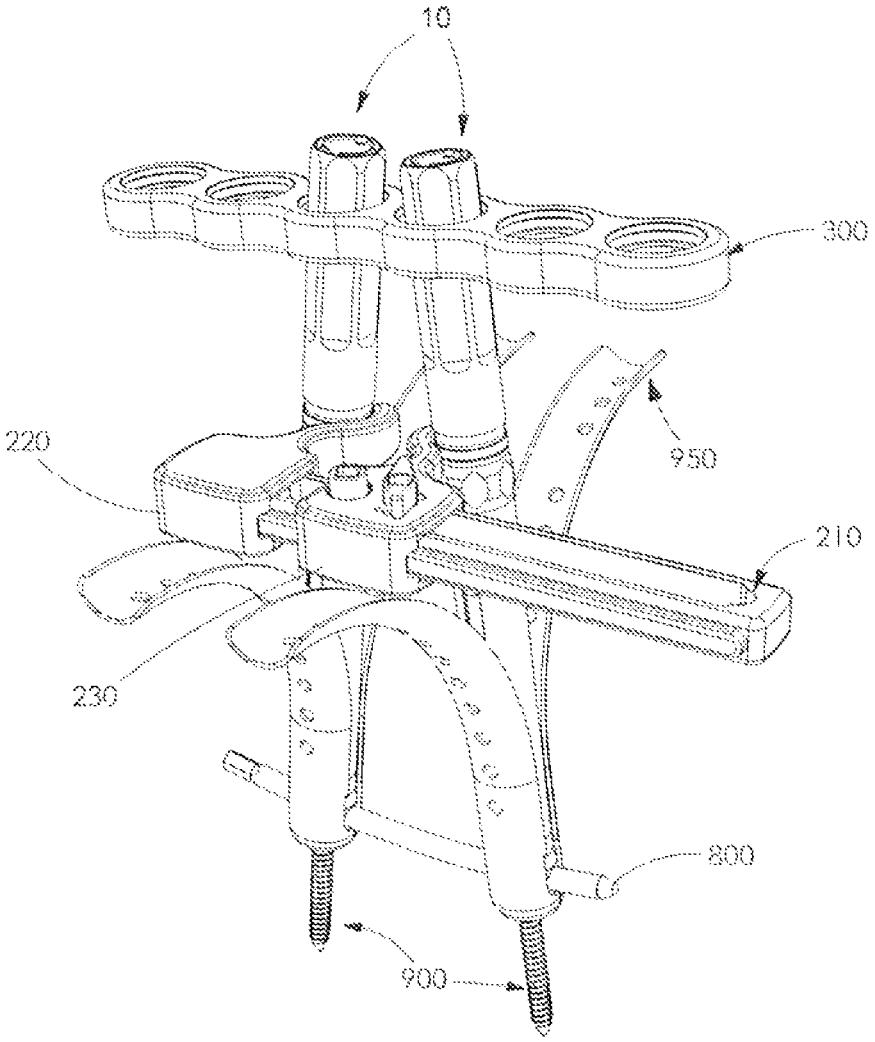
FIG. 9 is a perspective view of the compressor/distractor system of FIG. 8 in a distracting configuration.

Referring now to FIGS. 8 and 9, a compressor/distractor system 200 includes rod reducers 10, a compressor/distractor device 210, and a fulcrum 300. System 200 may further include one or more minimally invasive retraction devices 950, such as the retractor disclosed in U.S. Pat. No. 7,846,093, the entire contents of which is incorporated by reference. Each of the two rod reducers 10 engages a respective pedicle screw 900. Each pedicle screw 900 is inserted into a respective vertebra and is configured to receive spinal rod 800 in saddle portion 912 as shown in FIG. 1C. Compressor/distractor device 210 is configured for selective engagement with each rod reducer 10 when each rod reducer 10 is attached to pedicle screw 900.

Figure 10A:
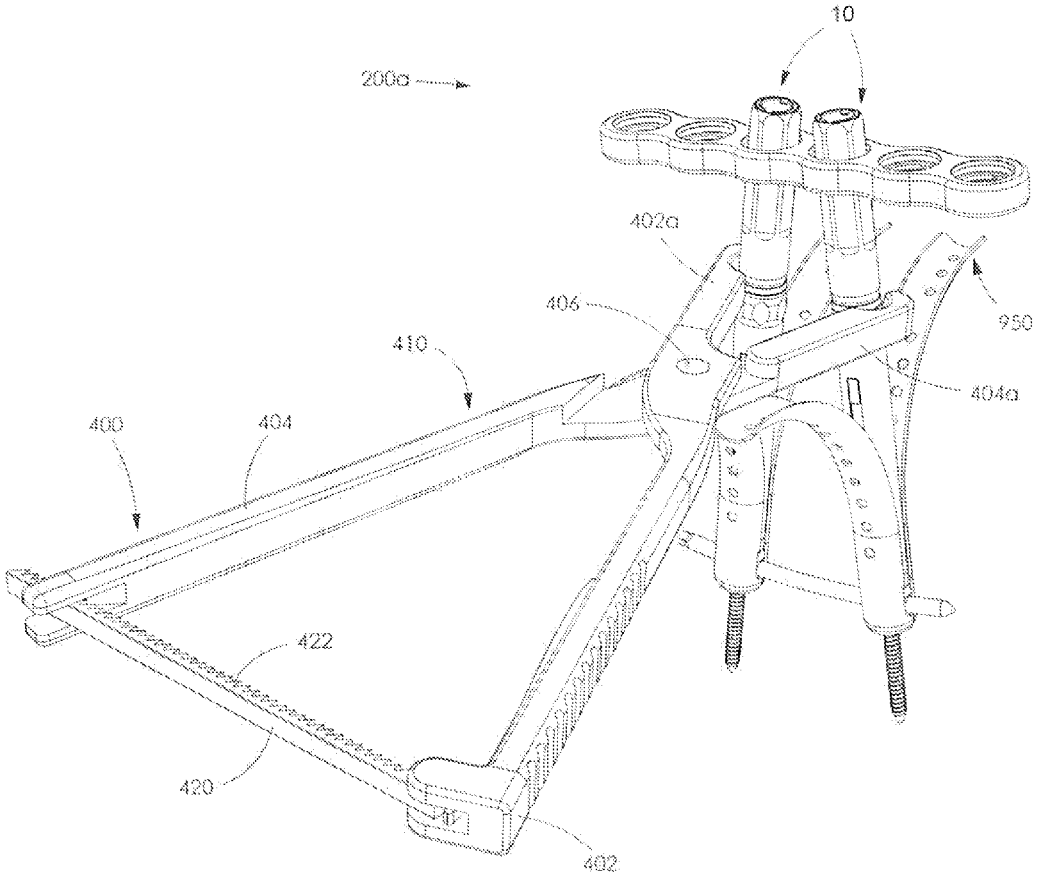
FIG. 10A is a perspective view of another embodiment of a compressor/distractor system in accordance with the principles of the present disclosure in a compressing configuration.
Figure 10B:
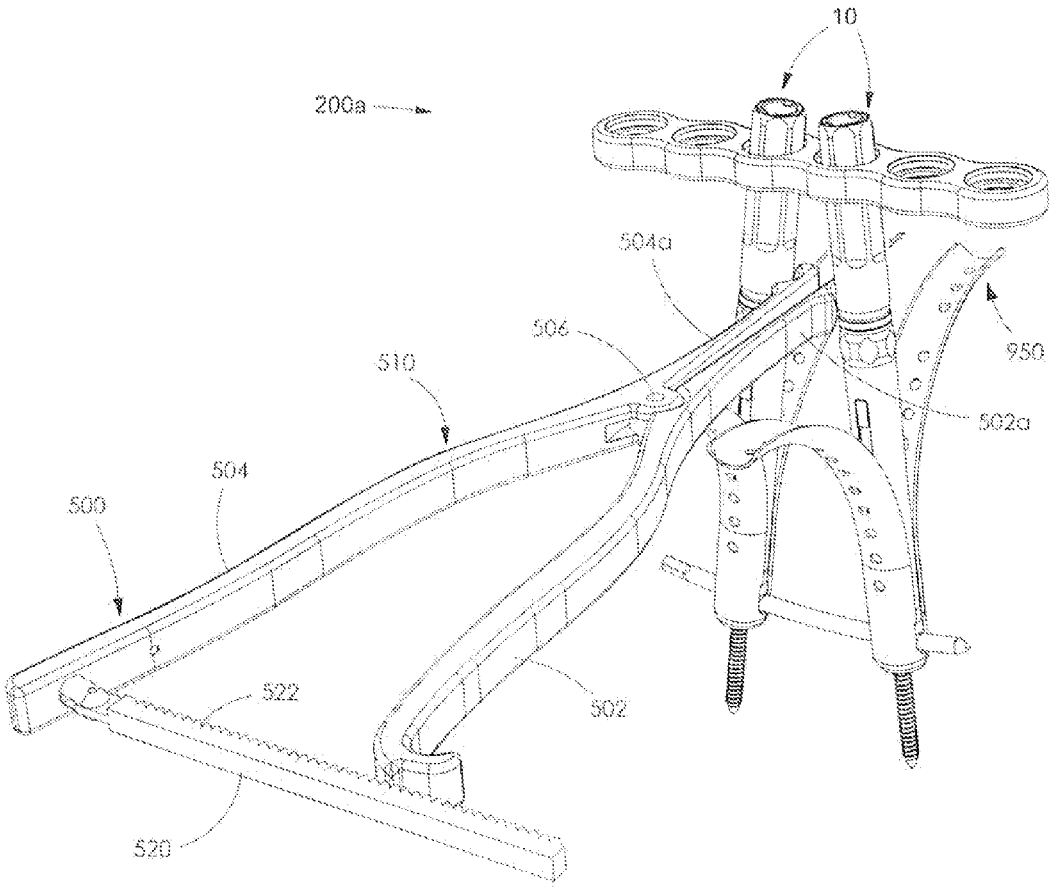
FIG. 10B is a perspective view of the compressor/distractor system of FIG. 10A in a distracting configuration.

FIGS. 10A and 10B illustrate other embodiments of compressor/distractor system 200a using compressor 400 and distractor 500 respectively as the force applying device. As shown in FIG. 10A, the compressor 400 has a handle assembly 410 with handles 402, 404 that are pivotably coupled together by pivot pin 406. Distal portions of handles 402, 404 have respective grippers 402a, 404a for engaging rod reducers 10. Each gripper 402a, 404a includes an arcuate recess configured for engaging an outer surface of rod reducer 10. Compressor 400 also includes an arm 420 having teeth 422 disposed thereon. Teeth 422 releasably engage a distal portion of handle 404 for maintaining a predetermined distance or spacing between handles 402, 404 during a compression stroke that moves rod reducers 10 towards each other. The arm 420 is pivotably coupled to a distal end of arm 402 such that it can be repositioned and allow handles 402, 404 to be moved away from each other once the desired amount of compression is achieved. Similarly, as shown in FIG. 10B, the distractor 500 has a handle assembly 510 with handles 502, 504 that are pivotably coupled together by pivot pin 506. Distal portions of handles 502, 504 have respective grippers 502a, 504a for engaging rod reducers 10. Each gripper 502a, 504a includes an arcuate recess configured for engaging an outer surface of rod reducer 10. Distractor 500 also includes an arm 520 having teeth 522 disposed thereon. Teeth 522 releasably engage a distal portion of handle 502 for maintaining a predetermined distance or spacing between handles 502, 504 during a distraction stroke that moves rod reducers 10 away from each other. The arm 520 is pivotably coupled to a distal end of arm 504 such that it can be repositioned and allow handles 502, 504 to be moved away from each other once the desired amount of distraction is achieved.

Figure 11A:
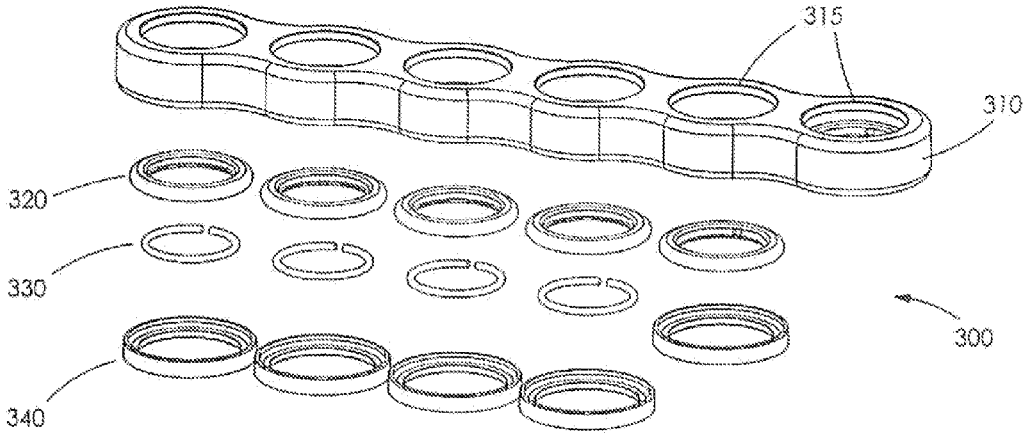
FIG. 11A is an exploded view of the fulcrum of FIG. 11.
Figure 11:
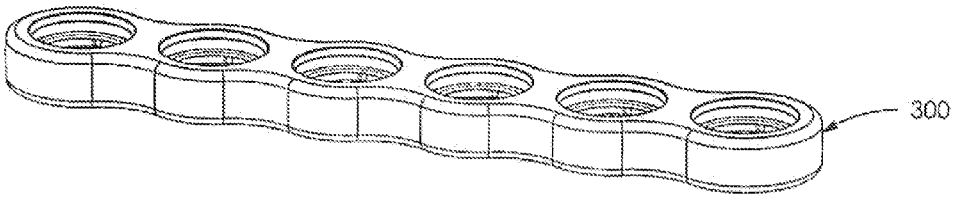
FIG. 11 is a perspective view of the fulcrum of FIG. 9.
Figure 11B:
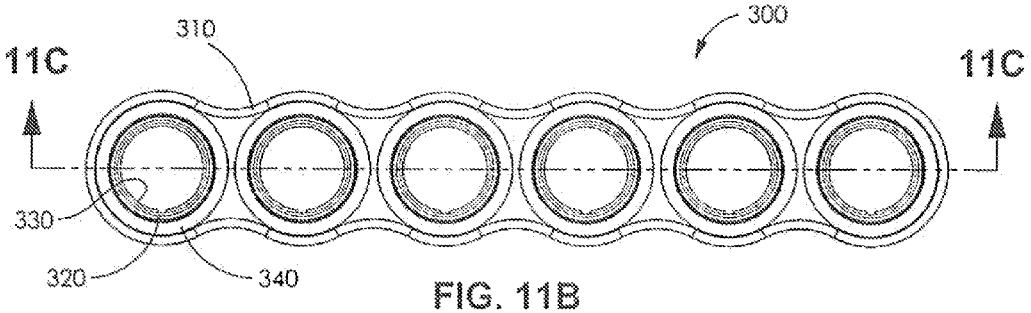
FIG. 11B is a top view of the fulcrum of FIG. 11.
Figure 11C:
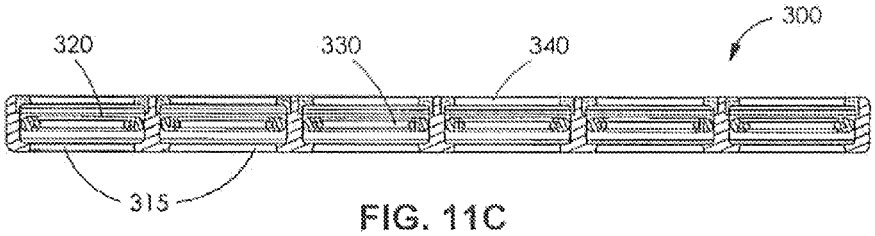
FIG. 11C is a side cross-sectional view of the fulcrum taken along the section line 11C-11C in FIG. 11B.

Now referring to FIGS. 11-11C illustrating fulcrum 300 including through holes 315 which receive inner bearing rings 320 which house retaining rings 330 that are prevented from falling out of fulcrum 300 by caps 340. Fulcrum 300 is an elongate structure and each through hole 315 includes an annular groove for retaining inner bearing rings 320 and their respective retaining rings 330.

Figure 13:
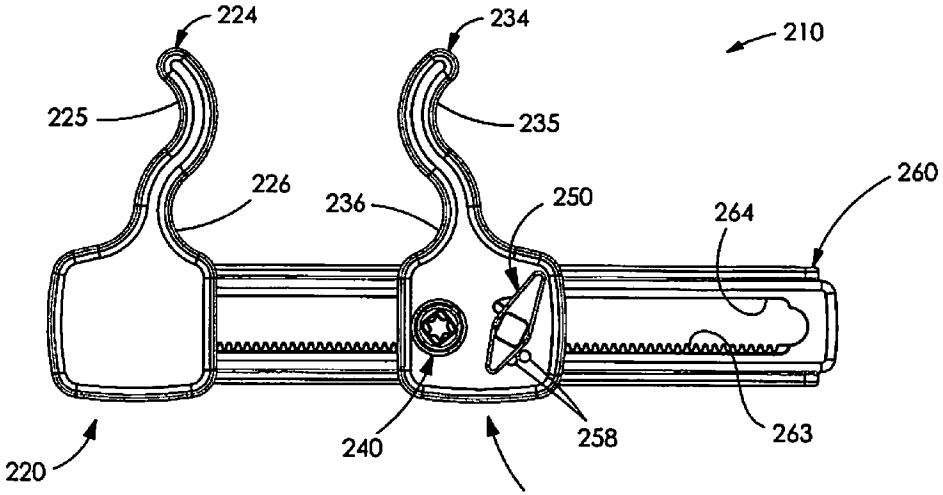
FIG. 13 is a top view of the compressor/distractor device of FIG. 12.
Figure 12:
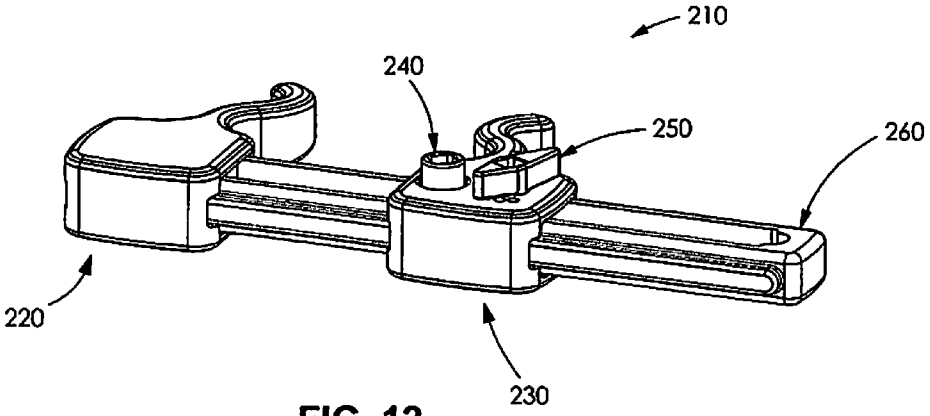
FIG. 12 is an enlarged view of the compressor/distractor device of FIG. 9.
Figure 14:
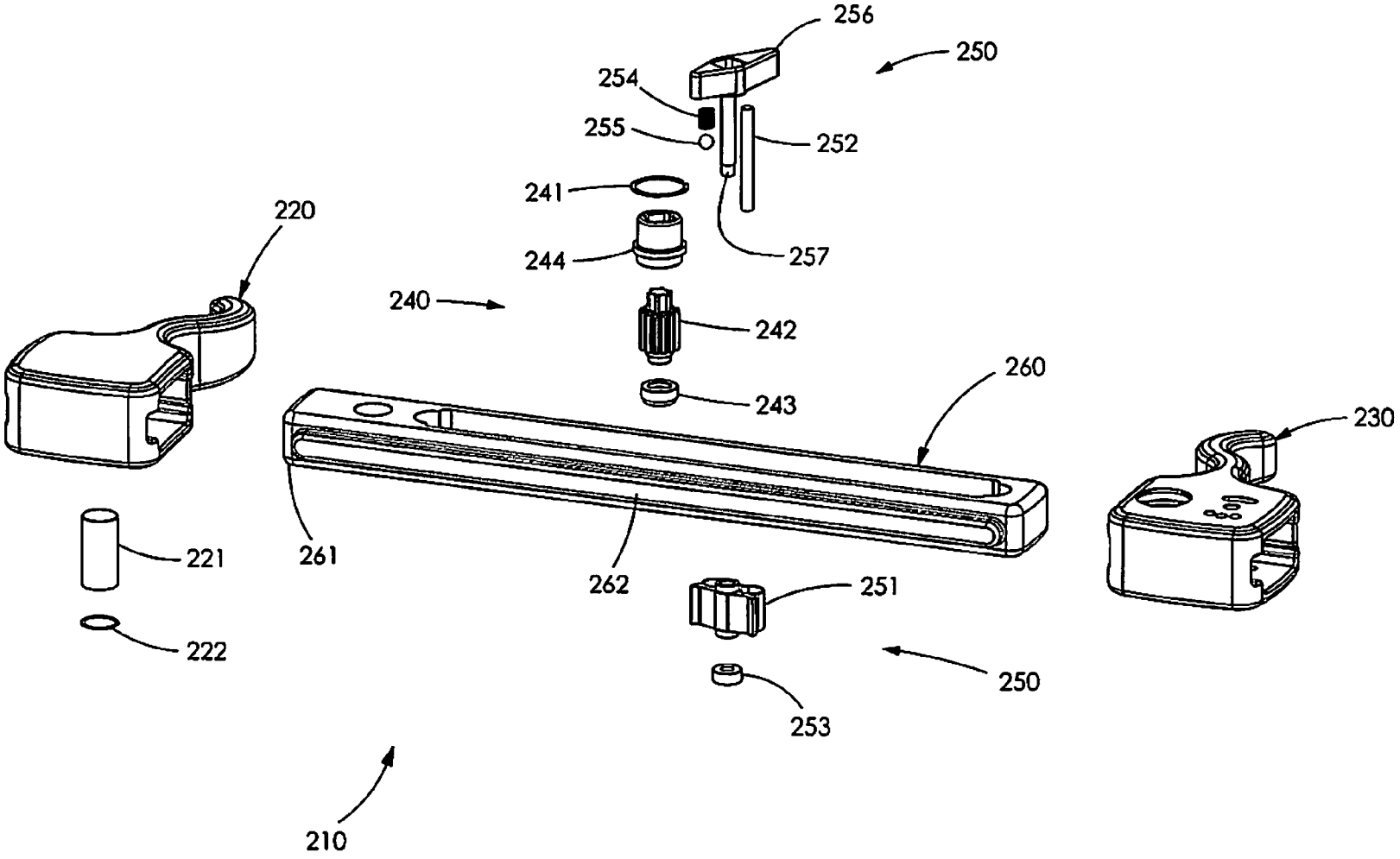
FIG. 14 is an exploded view of the compressor/distractor device of FIG. 12.

Referring now to FIGS. 12-14, compressor/distractor device 210 has a first hook member 220, a second hook member 230, and a body portion 260. Body portion 260 includes first end 261 and track 262 extending from first end 261 along a length of body portion 260. Track 262 includes a set of teeth 263 and sidewall 264. First end 261 is insertable into a recess of the first hook member 220 and is fixed in position at first end 261 of body portion 260 by the cooperation of retaining pin 221 and first end retaining ring 222.

First and second hook members 220, 230 may each include hook portions 224, 234 for engaging rod reducers 10. Hook portions 224, 234 have respective distracting hooks 225, 235 and compressing hooks 226, 236. When rod reducers 10 are between first and second hook members 220, 230, each compressing hook 226, 236 engages a rod reducer 10 in a compressing configuration of compressor/distractor device 210 (FIG. 8). When first and second hook members 220, 230 are between rod reducers 10, each distracting hook 225, 235 engages a rod reducer 10 in a distracting configuration of compressor/distractor device 210 (FIG. 9). Compressor/distractor device 210 may also have a neutral configuration. Each hook member 220, 230 may engage gripping features 22c of each rod reducer 10.

Second hook member 230 may include a switch assembly 250 and a gear assembly 240. Switch assembly 250 may include a pawl 251, a pawl switch pin 252, a switch cap 253, a spring 254, a ball 255, ball detents 258, a switch 256, and a switch shaft 257. Switch assembly 250 is selectable amongst a first condition, a second condition, and a third condition. Each condition may correspond to a configuration of the compressor/distractor device 210. In the first condition, switch assembly 250 restrains second hook member 230 from traversing track 262 towards the first hook member 220, while permitting second hook member 230 to traverse track 262 away from the first hook member 220 (i.e., a distracting configuration). In the second condition, switch assembly 250 restrains second hook member 230 from traversing track 262 away from the first hook member 220, while permitting second hook member 230 to traverse track 262 towards the first hook member 220 (i.e., a compressing configuration). In the third condition, switch assembly 250 allows the second hook member 230 to freely move along track 262 in either direction (i.e., a neutral configuration), which allows for quick adjustment of compressor/distractor device 210.

Switch 256 rotates about switch shaft 257 causing pawl pivot pin 252 to rotate pawl 251 about switch shaft 257. Pawl pivot pin 252 acts on pawl 251 causing pawl 251 to engage set of teeth 263 which restrains second hook member from traversing in the undesired direction.

Second hook member 230 may include ball detents 258. Each ball detent 258 corresponds to a position of switch 256. Switch 256 may be retained in each position by spring 254 pressing ball 255 into a corresponding ball detent 258. Ball 255 selectively engages each ball detent 258 when the switch is in one of the positions corresponding to the compressing, distracting, and neutral configurations of the compressor/distractor device 210.

Gear assembly 240 engages set of teeth 263 causing second hook member 230 to traverse track 262. Rotation of traversing screw 244 rotates pinion 242. The cooperation of pinion 242 with set of teeth 263 induces the second hook member 230 to traverse track 262. A drive tool (not shown) may engage and rotate traversing screw 244.

A method for using system 200 to manipulate a vertebra into a desired position with respect to a second vertebra is discussed below. First, a surgeon accesses the spinal area of a patient having at least two pedicle screws 900 secured to adjacent vertebrae (not shown). Each pedicle screw 900 may be engaged by a minimally invasive retraction device 950. The surgeon then engages each pedicle screw 900 with a rod reducer 10 by attaching inner member 30 to pedicle screw head 910 as shown in FIG. 1B. Each inner member 30 receives a respective pedicle screw head 910 between arms 32. Next, the surgeon advances an outer member 20 along each inner member 30 by rotating the distal segment 21 of the outer member 20. The surgeon may use handle assembly 650 to rotate distal segment 21.

Rod engaging slots 25 of proximal segment 22 of each outer member 20 receives a portion of rod 800 and advances rod 800 into saddle portion 912 of each pedicle screw 900 as shown in FIGS. 1B and 1C. Once each outer member 20 is fully advanced with respect to each inner member 30 as shown in FIG. 1C, the surgeon engages each outer member 20 with a force applying device 210, 400, 500 as shown in FIGS. 8-10B. The force applying device may include gear assembly 240. Then the surgeon inserts a set screw (not shown) through each rod reducer 10 for securing the rod 800 to each pedicle screw 900. The surgeon may rotate at least one of the set screws to either partially or fully secure rod 800 to at least one of the pedicle screws 900.

Then the surgeon manipulates gear assembly 240 until each pedicle screw 900 is in a desired position on rod 800. Manipulation of gear assembly 240 may include rotating traversing screw 244. The surgeon may use a drive tool to manipulate gear assembly 240.

Then the surgeon rotates each set screw to fully secure rod 800 to each pedicle screw 900 in the desired position. Then the surgeon may remove compressor/distractor device 210 and each rod reducer 10.

The surgeon may also attach fulcrum 300 to gripping portion 21b of proximal segment 21 of each outer member 20 before manipulating gear assembly 240. Fulcrum 300 may then be removed with the compressor/distractor device 210 and each of the rod reducers 10.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method for manipulating vertebrae comprising:

accessing the spinal area of a patient having a pedicle screw secured to each of at least two vertebrae;

engaging each pedicle screw with an inner member having distal and proximal ends defining a longitudinal axis therebetween, the distal end of each inner member receiving a head of the pedicle screw;

advancing an outer member having distal and proximal ends distally along each of the inner members by rotating the proximal end of each of the outer members relative to each inner member, a pair of receiving slots on the distal end of each outer member receiving a portion of a spinal rod, each pair of receiving slots advancing the spinal rod into a saddle portion of the head of each pedicle screw;

attaching a force applying device and a fulcrum to an outer surface of each outer member, the force applying device including first and second hook members and having a compressing configuration when the first and second hook members are attached to each outer member with each of the outer members between the first and second hook members and a distracting configuration when the first and second hook members are attached to each outer member with the first and second hook members between each of the outer members;

manipulating each outer member with the force applying device until each of the pedicle screws is in a desired position with respect to the spinal rod; and securing each pedicle screw to the spinal rod with a set screw.

2. The method of claim 1, wherein the force applying device further includes a neutral configuration and the second hook member includes a switch assembly having a first, a second, and a third position, each position corresponding to a configuration of the force applying device.

3. The method of claim 1, wherein the first and second hook members each include a hook portion, each hook portion having a compressing hook and a distracting hook.

4. The method of claim 1, wherein the fulcrum is attached to a gripping portion of each outer member.

5. The method of claim 1, wherein the step of advancing further includes attaching an anti-torque handle to a distal segment of each outer member and attaching a turning handle to a proximal segment of each outer member.

6. The method of claim 1, wherein the method further includes the step of inserting at least one set screw through an inner member and at least partially locking the rod to at least one of the pedicle screws before the step of manipulating the each outer member.

7. A method for manipulating vertebrae comprising:

securing a first elongate member to a first pedicle screw that is secured in a first vertebra;

securing a second elongate member to a second pedicle screw that is secured in a second vertebra; and manipulating the first and second elongate members with a force applying device until the first and second pedicle screws are in a desired position, the force applying device having first and second hook members, each hook member having a distracting hook and a compressing hook.

8. The method according [of] *to* claim 7, wherein manipulating the first and second elongate members with the force applying device includes positioning the first and second elongate members between the first and second hook members of the force applying device to compress the first and second elongate members towards one another.

9. The method according [of] *to* claim 7, wherein manipulating the first and second elongate members with the force applying device includes positioning the first and second hook members of the force applying device between the first and second elongate members to distract the first and second elongate members away from one another.

10. The method according [of] *to* claim 7, further comprising positioning a fulcrum over a [distal] *proximal* end of each of the first and second elongate members before manipulating the first and second elongate members with the force applying device.

11. The method according to claim 10, wherein manipulating the elongate members with the force applying device includes engaging the first elongate member with the first hook member between the fulcrum and the pedicle screw and engaging the second elongate member with the second hook member between the fulcrum and the pedicle screw.

12. The method according [of] *to* claim 7, further comprising:

reducing a spinal rod into a head of the first pedicle screw with the first elongate member; and reducing the spinal rod into a head of the second pedicle screw with the second elongate member.

13. A method for manipulating vertebrae comprising:

securing a first elongate member to a first pedicle screw that is secured in a first vertebra;

securing a second elongate member to a second pedicle screw that is secured in a second vertebra; and manipulating the first and second elongate members with a force applying device until the first and second pedicle screws are in a desired position, the force applying device having a compressing configuration, a distracting configuration, and a neutral configuration and including two hook members, at least one of the two hook members including switch assembly for selecting a respective one of the compressing, distracting, and neutral configurations, the switch assembly defining detents which each correspond to a respective one of the compressing, distracting, and neutral configurations of the force applying device.

*14. The method according to claim 10, wherein positioning the fulcrum over the proximal end of each of the first and second elongate members comprises positioning each of the first and second elongate members in a respective through hole of a plurality of through holes extending through the fulcrum.*

*15. The method according to claim 14, wherein the plurality of through holes extending through the fulcrum includes multiple through holes for each of the first and second elongate members, the through holes being spaced apart from one another such that each of the first and second elongate members can be selectively received within different ones of the multiple through holes, so as to thereby define a variable spacing between the first and second elongate members at a location where the fulcrum receives the first and second elongate members.*

*16. The method according to claim 15, wherein the plurality of first and second through holes are aligned along an axis of the fulcrum, the through holes being spaced apart along the axis.*

*17. The method according to claim 14, wherein each of the plurality of through holes includes a bearing ring received within the respective through hole.*

*18. The method of claim 1, wherein the fulcrum includes a plurality of through holes configured to receive each of the outer members therein.*

*19. The method of claim 18, wherein the plurality of through holes in the fulcrum includes multiple through holes for each of the outer members, the through holes being spaced apart from one another such that each outer member can be selectively received within different ones of the multiple through holes, so as to thereby define a variable spacing between the outer members at a location where the fulcrum receives the outer members.*

*20. The method of claim 19, wherein the plurality of through holes are aligned along an axis of the fulcrum, the through holes being spaced apart along the axis.*

*21. The method of claim 18, wherein each of the plurality of through holes includes a bearing ring received within the respective through hole.*

*22. The method of claim 13, further comprising engaging the first and second elongate members with a fulcrum by positioning each of the first and second elongate members in a respective through hole of a plurality of through holes extending through the fulcrum.*

*23. The method of claim 22, wherein the plurality of through holes extending through the fulcrum includes multiple through holes for each of the first and second elongate members, the through holes being spaced apart from one another such that each of the first and second elongate members can be selectively received within different ones of the multiple through holes, so as to thereby define a variable spacing between the first and second elongate members at a location where the fulcrum receives the first and second elongate members.*

*24. The method of claim 23, wherein the plurality of first and second through holes are aligned along an axis of the fulcrum, the through holes being spaced apart along the axis.*

*25. The method of claim 22, wherein each of the plurality of through holes includes a bearing ring received within the respective through hole.*

*26. A method for manipulating vertebrae comprising:*

*securing a first elongate member to a first pedicle screw that is secured in a first vertebra;*

*securing a second elongate member to a second pedicle screw that is secured in a second vertebra;*

*selecting a selected spacing from a plurality of different possible spacings provided by a fulcrum having a plurality of receptacles configured to receive the first and second elongate members therein, the spacings each being characterized by a length dimension defined between any first one of the receptacles and any second one of the receptacles, such that the selected spacing is defined by the length dimension between a selected first one of the receptacles and a selected second one of the receptacles;*

*engaging the first and second elongate members with the fulcrum by receiving the first elongate member within the selected first one of the receptacles and receiving the second elongate member within the selected second one of the receptacles so as to fix a distance between the first and second elongate members at a fulcrum location along the first and second elongate members, the distance being the length dimension defined between the selected first one of the receptacles and the selected second one of the receptacles; and*

*applying compression and/or distraction forces to the first and second elongate members while the fulcrum fixes the distance between the first and second elongate members at the fulcrum location.*

*27. The method of claim 26, wherein the first and second receptacles are through holes extending through the fulcrum.*

*28. The method of claim 26, wherein the plurality of first and second receptacles are aligned along an axis of the fulcrum, the receptacles being spaced apart along the axis.*

*29. The method of claim 26, wherein each of the plurality of first and second receptacles includes a bearing ring received therein.*

*30. The method of claim 26, wherein each of the first and second elongate members is a rod reducer.*

*31. The method of claim 26, wherein each of the plurality of different possible spacings provided by the fulcrum corresponds to a different respective angle defined between the first and second elongate members when the first and second elongate members are secured to the respective first and second pedicle screws and when the first and second members are engaged with the fulcrum at the fulcrum location.*

*32. The method of claim 26, wherein the step of applying compression and/or distraction forces to the first and second elongate members comprises engaging a force applying device to the first and second elongate members, the force applying device being engageable to a plurality of force applying locations on each of the first and second elongate members.*

*33. The method of claim 32, wherein the step of engaging the force applying device to the first and second elongate members comprises engaging the force applying device to the first and second elongate members at a selected one of the force applying locations, the selected force applying location being between the fulcrum and the first and second pedicle screws.*

*34. The method of claim 26, wherein the fulcrum is engageable with the first and second elongate members by receiving the first and second elongate members at a variety of different fulcrum locations along a respective portion of each of the first and second elongate members.*

* * * * *